(12) United States Patent
Updyke et al.

(10) Patent No.: US 8,889,004 B2
(45) Date of Patent: Nov. 18, 2014

(54) DIALYSIS SYSTEMS AND METHODS

(75) Inventors: Palmer David Updyke, Walnut Creek, CA (US); Harold Frederick Sandford, Groton, MA (US); Benjamin Joseph Lipps, Boston, MA (US); Douglas Mark Zatezalo, Allison Park, PA (US); Michael James Beiriger, Pittsburgh, PA (US); James Matthew Mullner, Hudson, OH (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 265 days.

(21) Appl. No.: 12/844,968

(22) Filed: Jul. 28, 2010

(65) Prior Publication Data

US 2011/0017665 A1 Jan. 27, 2011

Related U.S. Application Data

(63) Continuation-in-part of application No. 12/271,359, filed on Nov. 14, 2008.

(60) Provisional application No. 61/003,429, filed on Nov. 16, 2007.

(51) Int. Cl.
| | |
|---|---|
| *B01D 61/26* | (2006.01) |
| *A61M 37/00* | (2006.01) |
| *B01D 61/28* | (2006.01) |
| *A61M 1/16* | (2006.01) |
| *A61M 1/28* | (2006.01) |
| *A61M 1/34* | (2006.01) |

(52) U.S. Cl.
CPC ............. *A61M 1/1696* (2013.01); *A61M 1/28* (2013.01); *A61M 1/3472* (2013.01); *A61M 2209/082* (2013.01)

USPC ................ 210/321.71; 210/646; 604/5.01; 604/5.04; 604/29; 604/3.019

(58) Field of Classification Search
None
See application file for complete search history.

(56) References Cited

U.S. PATENT DOCUMENTS

| | | | |
|---|---|---|---|
| 3,871,913 | A | 3/1975 | Shaldon |
| 4,174,231 | A | 11/1979 | Hobgood |
| 4,191,351 | A | 3/1980 | Goyne |
| 4,581,141 | A | 4/1986 | Ash |
| 4,666,598 | A | 5/1987 | Heath et al. |
| 4,684,460 | A | 8/1987 | Issautier |

(Continued)

FOREIGN PATENT DOCUMENTS

| | | |
|---|---|---|
| EP | 0 278 100 | 8/1988 |
| EP | 0 673 658 | 9/1995 |

(Continued)

OTHER PUBLICATIONS

"RX Guide to Custom Dialysis," COBE Renal Care Inc., Revision E. Sep. 1993.

(Continued)

*Primary Examiner* — Krishnan S Menon
(74) *Attorney, Agent, or Firm* — Fish & Richardson P.C.

(57) ABSTRACT

This disclosure generally relates to dialysis systems and related methods. In one aspect of the invention, a dialysis system includes a device configured so that a medical fluid can pass therethrough, and the device is adapted to remove one or more substances from the medical fluid as the medical fluid passes through the device. The dialysis system can also include a sodium control system adapted to alter a sodium concentration of the medical fluid.

19 Claims, 6 Drawing Sheets

(56) References Cited

U.S. PATENT DOCUMENTS

| | | | |
|---|---|---|---|
| 4,728,496 | A | 3/1988 | Petersen et al. |
| 4,770,787 | A | 9/1988 | Heath et al. |
| 4,784,495 | A | 11/1988 | Jonsson et al. |
| 4,789,467 | A | 12/1988 | Lindsay et al. |
| 4,997,577 | A | 3/1991 | Stewart |
| 5,256,371 | A | 10/1993 | Pippert |
| 5,262,068 | A | 11/1993 | Bowers et al. |
| 5,277,820 | A | 1/1994 | Ash |
| 5,304,349 | A | 4/1994 | Polaschegg |
| 5,409,612 | A | 4/1995 | Maltais et al. |
| 5,421,813 | A | 6/1995 | Ohnishi |
| 5,536,412 | A | 7/1996 | Ash |
| 5,589,070 | A | 12/1996 | Maltais et al. |
| 5,591,344 | A | 1/1997 | Kenley et al. |
| 5,603,902 | A | 2/1997 | Maltais et al. |
| 5,605,630 | A | 2/1997 | Shibata |
| 5,713,125 | A | 2/1998 | Watanabe et al. |
| 5,788,099 | A | 8/1998 | Treu et al. |
| 5,919,369 | A | 7/1999 | Ash |
| 5,944,684 | A | 8/1999 | Roberts et al. |
| 6,000,567 | A | 12/1999 | Carlsson et al. |
| 6,036,858 | A | 3/2000 | Carlsson et al. |
| 6,086,753 | A | 7/2000 | Ericson et al. |
| 6,143,181 | A | 11/2000 | Falkvall et al. |
| 6,170,785 | B1 | 1/2001 | Lampropoulos |
| 6,190,855 | B1 | 2/2001 | Herman et al. |
| 6,277,277 | B1 | 8/2001 | Jacobi et al. |
| 6,280,632 | B1 | 8/2001 | Polaschegg |
| 6,308,721 | B1 | 10/2001 | Bock et al. |
| 6,409,699 | B1 | 6/2002 | Ash |
| 6,416,293 | B1 | 7/2002 | Bouchard et al. |
| 6,428,706 | B1 | 8/2002 | Rosenqvist et al. |
| 6,484,383 | B1 | 11/2002 | Herklotz |
| 6,672,841 | B1 | 1/2004 | Herklotz et al. |
| 6,743,201 | B1 | 6/2004 | Dönig et al. |
| 6,755,976 | B2 | 6/2004 | Rosenqvist et al. |
| 6,878,283 | B2 | 4/2005 | Thompson |
| 7,033,498 | B2 | 4/2006 | Wong |
| 7,077,956 | B2 | 7/2006 | Rovatti |
| 7,241,272 | B2 | 7/2007 | Karoor et al. |
| 7,789,849 | B2 | 9/2010 | Busby et al. |
| 7,947,179 | B2 | 5/2011 | Rosenbaum et al. |
| 8,192,387 | B2 | 6/2012 | Brugger et al. |
| 8,235,931 | B2 | 8/2012 | Burbank et al. |
| 2002/0079695 | A1 | 6/2002 | Campbell et al. |
| 2003/0105424 | A1 | 6/2003 | Karoor et al. |
| 2004/0019312 | A1 | 1/2004 | Childers |
| 2004/0050789 | A1 | 3/2004 | Ash |
| 2005/0274658 | A1 | 12/2005 | Rosenbaum et al. |
| 2007/0158247 | A1 | 7/2007 | Carr et al. |
| 2007/0158249 | A1 | 7/2007 | Ash |
| 2007/0158268 | A1 | 7/2007 | DeComo |
| 2007/0161113 | A1 | 7/2007 | Ash |
| 2007/0161941 | A1 | 7/2007 | Ash et al. |
| 2007/0181499 | A1 | 8/2007 | Roberts et al. |
| 2008/0149563 | A1 | 6/2008 | Ash |
| 2008/0177216 | A1 | 7/2008 | Ash |
| 2008/0200869 | A1 | 8/2008 | Bedingfield |
| 2009/0107902 | A1 | 4/2009 | Childers |
| 2009/0114595 | A1 | 5/2009 | Wallenas et al. |
| 2011/0303588 | A1 | 12/2011 | Kelly et al. |

FOREIGN PATENT DOCUMENTS

| | | |
|---|---|---|
| EP | 0947814 A2 | 10/1999 |
| EP | 1 195 171 | 4/2002 |
| EP | 1 342 480 | 9/2003 |
| EP | 1 096 991 | 6/2004 |
| JP | 2004209103 | 7/2004 |
| WO | WO 97/02055 | 1/1997 |
| WO | WO 97/02056 | 1/1997 |
| WO | WO 98/17333 | 4/1998 |
| WO | WO 99/37342 | 7/1999 |
| WO | WO 02/30267 | 4/2002 |
| WO | WO 02/43859 | 6/2002 |
| WO | WO 2005/123230 | 12/2005 |
| WO | WO2006088419 A2 | 8/2006 |
| WO | WO 2007/028056 | 3/2007 |
| WO | WO2006036876 A8 | 4/2007 |
| WO | WO 2007/081383 | 7/2007 |
| WO | WO 2007/081384 | 7/2007 |
| WO | WO 2007/081565 | 7/2007 |
| WO | WO 2007/081576 | 7/2007 |

OTHER PUBLICATIONS

"*Sorbent Dialysis Pimer*," COBE Renal Care, Inc., Sep. 4, 1993 Ed.
Blumenkrantz et al., "*Artif Organs*," 3(3):230-236, 1978.
Operator's Manual—Fresenius 2008K Hemodialysis Machine (2000).
Sleep Safe Operating Instructions, Part 677 805 1, Fresenius Medical Care, 1st edition, Aug. 2000, 133 pages.
Sleep Safe Technical Manual, Part 677 805 1, Fresenius Medical Care, 1st edition, Aug. 2000, 174 pages.

DIALYSIS SYSTEMS AND METHODS

CROSS-REFERENCE TO RELATED APPLICATIONS

This application is a continuation-in-part application of and claims priority to U.S. application Ser. No. 12/271,359, filed on Nov. 14, 2008, which claims the benefit of U.S. Application Ser. No. 61/003,429, filed on Nov. 16, 2007. Each of the above-noted applications is incorporated by reference herein.

TECHNICAL FIELD

This disclosure relates to dialysis systems and methods.

BACKGROUND

Renal dysfunction or failure and, in particular, end-stage renal disease, causes the body to lose the ability to remove water and minerals and excrete harmful metabolites, maintain acid-base balance and control electrolyte and mineral concentrations within physiological ranges. Toxic uremic waste metabolites, including urea, creatinine, and uric acid, accumulate in the body's tissues which can result in a person's death if the filtration function of the kidney is not replaced.

Dialysis is commonly used to replace kidney function by removing these waste toxins and excess water. In one type of dialysis treatment—hemodialysis—toxins are filtered from a patient's blood externally in a hemodialysis machine. Blood passes from the patient through a dialyzer separated by a semi-permeable membrane from a large volume of externally-supplied dialysis solution. The waste and toxins dialyze out of the blood through the semi-permeable membrane into the dialysis solution, which is then discarded.

Hemodialysis treatments are typically conducted at a clinic since the hemodialysis machines generally require a continuous water source, reverse osmosis machinery, and drain lines for discarding the large volumes of water and dialysis solution used during a single treatment. Hemodialysis treatment typically must be performed three or four times a week, under supervision of the clinical staff, requirements that significantly decrease a patient's autonomy and quality of life.

Certain devices reconstitute used dialysis solution from hemodialysis and/or peritoneal dialysis as opposed to discarding it. The dialysis solution can be regenerated in a machine employing a device that eliminates urea from the solution. For example, the original Redy® (REcirculating DYalysis) Sorbent System (Blumenkrantz et al., Artif Organs 3(3):230-236, 1978) includes a sorbent cartridge having five layers through which dialysis solution containing uremic waste metabolites flows in order to be regenerated.

SUMMARY

In one aspect of the invention, a dialysis system includes a device configured so that a dialysis solution can pass therethrough, a fluid line in fluid communication with the device, and a sodium control system in fluid communication with the fluid line. The device is adapted to remove one or more substances from the dialysis solution as the dialysis solution passes through the device, and the sodium control system is adapted to alter a sodium concentration of solution passing through the fluid line.

In another aspect of the invention, a dialysis system includes a dialysis machine and a module connected to the dialysis machine. The module is configured to retain a device adapted to remove one or more substances from a dialysis solution as the dialysis solution passes through the device after exiting the dialysis machine. The module is configured to be releasably fluidly coupled to the dialysis machine and includes a sodium control system that is adapted to alter the sodium concentration of the dialysis solution. The sodium control system is arranged to alter the sodium concentration of the dialysis solution before the dialysis solution passes through the device.

In an additional aspect of the invention, a method includes removing one or more substances from spent dialysis solution by passing the spent dialysis solution through a device, and altering the sodium concentration of solution entering or exiting the device.

Embodiments can include one or more of the following features.

In some embodiments, the fluid line is arranged so that solution exiting the fluid line enters the device.

In some embodiments, the fluid line is arranged so that solution exiting the device enters the fluid line.

In some embodiments, the sodium control system is adapted to introduce a diluent (e.g., tap water) into the fluid line.

In some embodiments, the sodium control system includes a container that contains the diluent, and the sodium control system further includes a pump arranged to move the diluent from the container to the fluid line.

In some embodiments, the sodium control system is adapted to introduce sodium (e.g., a sodium chloride solution) into the fluid line.

In some embodiments, the sodium control system includes a container that contains a sodium solution, and the sodium control system further comprises a pump arranged to move the sodium solution from the container to the fluid line.

In some embodiments, the sodium control system further includes a diluent source, and the pump is arranged to move diluent from the diluent source to the fluid line.

In some embodiments, the sodium control system further includes one or more valves that can be actuated to control movement of the sodium solution and the diluent to the fluid line.

In some embodiments, the sodium control system is adapted to introduce a diluent and sodium into the fluid line.

In some embodiments, the dialysis system further includes a conductivity meter that is adapted to measure conductivity of the solution passing through the fluid line, and the conductivity meter is in communication with the sodium control system.

In some embodiments, the sodium control system is adapted to alter the sodium concentration of the solution passing through the fluid line based on an output signal of the conductivity meter.

In some embodiments, the sodium control system is adapted to decrease the sodium concentration of the solution passing through the fluid line if the output signal of the conductivity meter indicates a conductivity above a predetermined conductivity.

In some embodiments, the sodium control system is adapted to increase the sodium concentration of the solution passing through the fluid line if the output signal of the conductivity meter indicates a conductivity below a predetermined conductivity.

In some embodiments, the device is a sorbent cartridge.

In some embodiments, the sorbent cartridge includes at least one layer of material capable of purifying water and/or regenerating spent dialysis solution.

In some embodiments, a layer of the sorbent cartridge comprises sodium zirconium carbonate.

In some embodiments, the module comprises at least a portion of the sodium control system, and the device is fluidly coupled to the module.

In some embodiments, the dialysis machine is a hemodialysis machine.

In some embodiments, the module further includes a sodium control system that is adapted to alter the sodium concentration of the dialysis solution.

In some embodiments, the sodium control system is arranged to alter the sodium concentration of the dialysis solution before the dialysis solution passes through the device.

In some embodiments, the module can be releasably fluidly coupled to any of a plurality of different dialysis machines.

In some embodiments, the method includes altering the sodium concentration of solution entering the device.

In some embodiments, the method further includes passing the solution entering the device through a dialysis machine after altering the sodium concentration of the solution entering the device.

In some embodiments, the device is fluidly coupled to a module that is releasably fluidly coupled to a dialysis machine.

Embodiments can include one or more of the following advantages.

In some embodiments, the dialysis system can be used in a home environment. In particular, because the sorbent cartridge allows preparation of dialysate from tap water and enables spent dialysis to be recycled, the dialysis system does not require access to large volumes of water or dialysis solution, or necessitate expensive reverse osmosis devices, or require special plumbing or wiring. Thus, the dialysis system makes in home use much more practical compared to certain previous systems.

In some embodiments, the dialysis system controls sodium levels in the dialysis solution. In certain embodiments, for example, the spent dialysis solution is passed through a sorbent cartridge that removes toxins from the dialysis solution. The dialysis system can include a device upstream from the sorbent cartridge that delivers sodium (e.g., sodium chloride (NaCl)) into the dialysis solution to maintain sodium levels within a desired range. Maintaining sodium levels in the dialysis solution within a desired range can help to reduce discomfort experienced by the patient as a result of increased or decreased sodium levels in the patient's blood.

In certain embodiments, a sensor (e.g., conductivity meter) is arranged downstream of the cartridge and is connected to the sodium control system. The sodium control system can make adjustments to the sodium levels in the dialysis solution based on signals received from the sensor. As a result, the sensor can ensure the sodium level in the dialysis solution is within a desired range before the dialysis solution is delivered to the patient.

In certain embodiments, sensors (e.g., conductivity meters) are located both upstream and downstream of the cartridge. The sodium control system can make adjustments to the sodium levels in the dialysis solution based on signals received from the sensors. These sensors provide information about the conductivity at multiple locations along the fluid path, allowing the conductivity to be monitored, adjusted, and controlled more precisely.

Other aspects, features, and advantages will be apparent from the description and drawings, and from the claims.

DETAILED DESCRIPTION

This disclosure generally relates to dialysis systems and methods. The dialysis systems typically include a module that is capable of regenerating dialysis solution (e.g., dialysate). The module typically includes a sorbent device for filtering used or spent dialysis solution and a sodium control system located upstream of the sorbent device for controlling sodium levels within the dialysis solution. By positioning the sodium control system upstream of the sorbent device, tap water can be used to create sodium chloride solution and dilution water that is introduced to the dialysis solution to control sodium levels.

The systems and methods described herein can advantageously eliminate the high volume of water usage, expensive and noisy reverse osmosis equipment, and the need for a drain line that occur with many known dialysis systems and methods. Thus, the systems and methods described herein can enable a hemodialysis machine to be relatively easily modified for use in a home environment without requiring the installation of special plumbing or wiring in a patient's home. In addition, the systems and methods described herein can allow levels of sodium in the dialysis solution to be maintained within substantially the same physiological range as is achieved in single-pass hemodialysis.

Figure 1:
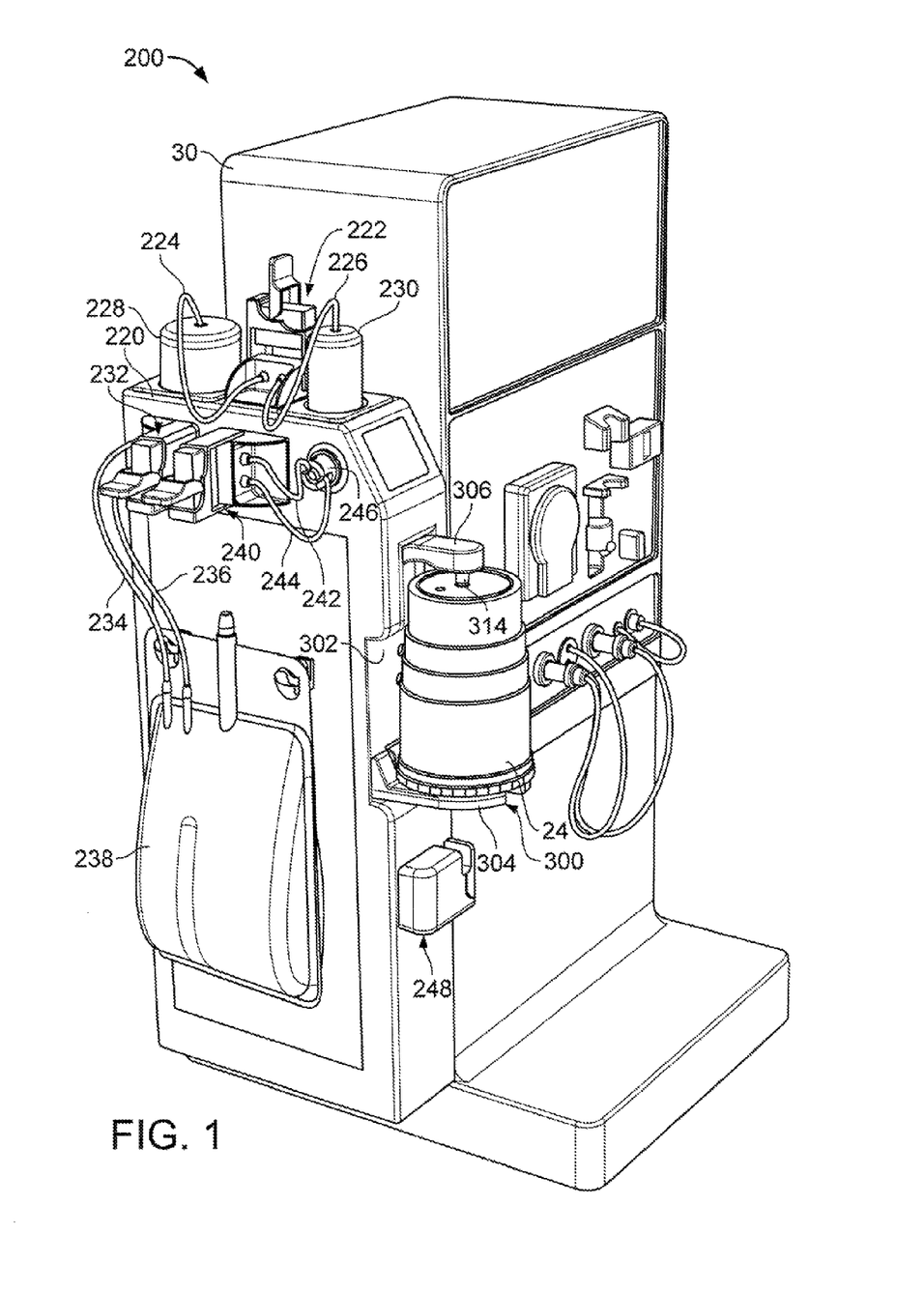
FIG. 1 is a perspective view of a dialysis system that includes a dialysis machine and a module with a sorbent cartridge holder that is holding a sorbent cartridge.

FIG. 1 shows a dialysis system 200 that includes a module 220 fluidly coupled to a dialysis machine 30. The module 220 includes a sorbent cartridge holder 300 configured to hold a sorbent cartridge 24. The module 220 also includes a manifold 222 to which fluid lines 224, 226 extending from an infusate container 228 and a sodium chloride container 230 are connected, a manifold 232 to which fluid lines 234, 236 extending from a dialysate bag or reservoir 238 are connected, and a manifold 240 to which fluid lines 242, 244 extending from an ammonium ($NH_4^+$) sensor 246 are connected. The module 220 further includes a manifold 248 that can be used to fluidly connect other components, such as a priming solution bag, a rinsing solution bag, a cleaning solution bag, and/or a drain bag to the module 220. Each of manifolds 222, 232, 240, and 248 can, for example, include projections on which fluid lines can be positioned to connect the various components described above to their respective manifold. Any of various other suitable connection mechanisms can alternatively or additionally be used to connect the fluid lines to the manifolds.

When in an open position, as shown in FIG. 1, the manifold 222 permits an infusate solution (e.g., a solution including magnesium, calcium, and potassium) and a sodium chloride solution to be delivered into fluid circulating through the module 220. Pumps and valves within the module 220 can, for example, be activated to pump the infusate solution and sodium chloride into the fluid circulating within the module 220. Similarly, the manifold 232 allows fluid to be transferred from the module 220 to the bag 238 and vice versa. Using pumps and valves within the module 220, fluid can be pumped into and suctioned out of the bag 238 via the fluid line 234 connected to the manifold 232. The manifold 240 permits fluid to be transferred from the module 220 to the ammonium sensor 246 and vice versa. By activating pumps and valves within the module 220 in a desired manner, the fluid can be pumped from the module 220 to the ammonium sensor 246 and can be drawn back to the module 220 from the ammonium sensor 246. The manifold 248 can also be placed in an open configuration during use and connected to fluid lines such that by activating pumps and valves within the module, fluid can be drawn into the module 220 from a bag (e.g., a priming solution bag, a rinsing solution bag, a cleaning solution bag) and/or pumped from the module into a bag (e.g., a drain bag). With the sorbent cartridge 24 fluidly connected to the cartridge holder 300, as shown in FIG. 1, fluid circulating within the module 220 is allowed to pass through the sorbent cartridge 24.

During dialysis treatment, the module 220 is configured in the manner shown in FIG. 1 to permit fluid communication between the fluid circulating within the module 220 and the sorbent cartridge 24, the infusate container 228, the sodium chloride container 230, the dialysate bag 238, the ammonium sensor 246, and, in some cases, one or more additional bags that can be connected to the module 220 via the manifold 248.

Figure 2:
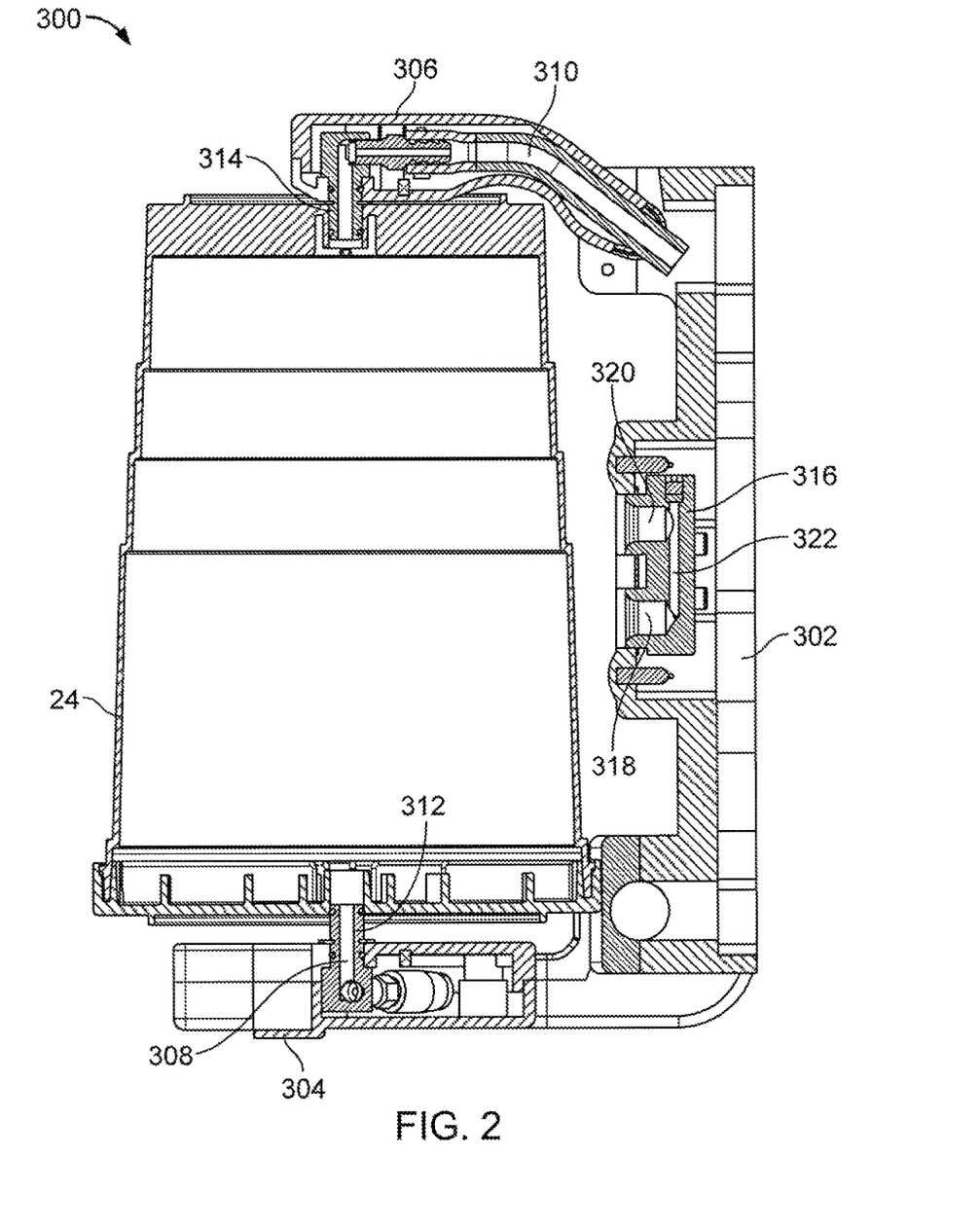
FIG. 2 is a cross-sectional view of the sorbent cartridge holder of FIG. 1 with a sorbent cartridge positioned in the sorbent cartridge holder.

FIG. 2 is a cross-sectional view of the cartridge holder 300 holding the sorbent cartridge 24. As shown in FIGS. 1 and 2, the cartridge holder 300 includes a back 302, a base 304 that is pivotably connected to a bottom portion of the back 302, and an arm 306 that is pivotably connected to a top portion of the back 302. The sorbent cartridge 24 can be positioned between and held in position by the base 304 and the arm 306. Referring to FIG. 2, fluid passageways 308, 310 extend through the base 304 and the arm 306, respectively. The base 304 and the arm 306 also include fittings (e.g., male nipples) 312, 314 that cooperate with the sorbent cartridge 24 to place the fluid passageways 308, 310 of the base 304 and the arm 306 in fluid communication with an interior chamber of the sorbent cartridge 24 and to help retain the sorbent cartridge 24 in position between the base 304 and the arm 306. This configuration permits fluid to pass through the fluid passageway 308 of the base 304 and into the interior chamber of the sorbent cartridge 24. The fluid can pass through the sorbent cartridge 24 and into the fluid passageway 310 of the arm 306. The base 304 and/or the arm 306 can be spring loaded. This can help the base 304 and the arm 306 to retain the sorbent cartridge 24 while also permitting the base 304 and the arm 306 to rotate about their hinged axes in the event that the sorbent cartridge 24 expands or contracts (e.g., in response to fluid retention and fluid pressure therein) during use. The fluid passageways 308, 310 of the base 304 and the arm 306 are connected to fluid lines within the module 220 such that the cartridge holder 300 can receive fluid (e.g., spent dialysis solution) from the module 220 and return fluid (e.g., recycled dialysis solution) to the module 220.

Referring again to FIG. 1, during dialysis, as discussed in greater detail below, spent dialysis solution is moved from the dialysis machine 30 into the module 220 where it passes through the sorbent cartridge 24, and then the recycled dialysis solution exiting the sorbent cartridge 24 is moved back to the dialysis machine 30. As the spent dialysis solution is passed through the sorbent cartridge 24, toxins, such as urea, and other substances, such as calcium, magnesium, and potassium are stripped from the spent dialysis solution. Sodium may also be stripped from the spent dialysis solution during the initial part of the treatment or, in certain cases, added to the spent dialysis solution as the spent dialysis solution passes through the sorbent cartridge 24 during the later part of the treatment. To compensate for these materials being stripped from the dialysis solution, calcium, magnesium, potassium, and sodium levels of the recycled dialysis solution can be altered (e.g., by introducing calcium, magnesium, potassium, sodium, and/or a diluent into the dialysis solution) to restore concentrations of those substances to desired levels. As the recycled dialysis solution then passes through a dialyzer in the dialysis machine 30, toxins are transferred from the patient's blood into the dialysis solution, forming spent dialysis solution. This spent dialysis solution is then circulated through the module 220 again to recycle or regenerate the spent dialysis solution. This process can be repeated until a desired amount of toxins have been removed from the patient's blood. Because the dialysis solution is recycled during the treatment as opposed to simply being discarded, the volume of dialysis solution used during the treatment can be substantially reduced relative to certain conventional hemodialysis techniques. In addition, maintaining the concentration of the various substances within the dialysis solution, such as calcium, magnesium, potassium, and sodium, can help to prevent the patient from experiencing discomfort during the treatment.

The sorbent device 24 includes a housing containing a sorbent cartridge capable of removing uremic toxins. In some embodiments, the cartridge is disposable. The cartridge can, for example, be constructed such that it can be disposed after use and removed from the housing. The replaced cartridge could then be replaced with a similar cartridge for a subsequent use of the module 20. The cartridge can purify water and regenerate spent dialysis solution through the use of a series of layers which can remove heavy metals (e.g., lead, mercury, arsenic, cadmium, chromium and thallium), oxidants (e.g., chlorine and chloramine), urea, phosphate and other uremic waste metabolites (e.g., creatinine and uric acid) from the solution, without removing or adsorbing excessive amounts of cations (e.g., calcium, magnesium, sodium, potassium) or essential ions.

In some embodiments, the components of the cartridge that perform the afore-mentioned functions include a purification layer that includes activated carbon; an ion exchange layer that includes a polymer phosphate binder or an ion exchange sorbent; and a urea removal layer that includes strong acid cation exchange resin and basic resin(s) or urea-degrading enzymes and an ion exchange sorbent together with a composition that rejects cations (e.g., flat membrane/hollow fibers described further herein, an ion-exchange membrane, or an encapsulation surrounding the urea removal components).

In certain embodiments, the cartridge includes the following layers and materials: sodium zirconium carbonate or other alkali metal-Group IV metal-carbonate; zirconium phosphate or other ammonia adsorbents; alumina or other like material; alumina supported urease or other immobilized enzyme layer or other material to convert urea to ammonia, such as diatomaceous earth or zirconium oxide; and granular activated carbon, such as charcoal, or other adsorbent. The sodium zirconium carbonate component can act as a phosphate adsorbent. The zirconium oxide can be capable of acting as a counter ion or ion exchanger to remove phosphate, and can be in the form of hydrous zirconium oxide (e.g., hydrous zirconium oxide containing acetate). The zirconium oxide can also be blended with the sodium zirconium carbonate when positioned in the cartridge.

Non-limiting examples of urea-degrading enzymes that can be employed in either embodiment of the sorbent cartridge include enzymes that are naturally occurring (e.g. urease from jack beans, other seeds or bacteria), produced by recombinant technology (e.g., in bacterial, fungal, insect or mammalian cells that express and/or secrete urea-degrading enzymes) or produced synthetically (e.g., synthesized). In some embodiments, the enzyme is urease.

In certain embodiments, the sorbent cartridge further includes hollow fibers. The hollow fibers can reject positively charged ions, as well as increase the capacity of the cartridge. The hollow fibers can be coated with an ion-rejecting material, which through a water-purification like mechanism allows the urea through but rejects positively charged ions such as calcium and magnesium. The material coating the hollow fibers can be any such material known to one of skill in the art (e.g., fatty acids or polymer chains like polysulfone) that can effectively reject calcium and magnesium and therefore retain the ions in the dialysis solution. Generally, to have this effect the material itself would be positively charged. In some embodiments, for example, the material used to coat the hollow fibers is cellulose acetate (e.g., cellulose triacetate). The hollow fibers that are to be coated are commercially available (e.g., Fresenius Medical Care North America) and can be coated with any desired ion-rejecting material available to one having skill in the art.

Alternatively, the hollow fibers can include an ion-selective nanofiltration membrane. Such membranes are commercially available from a number of sources (e.g., Amerida, Koch, GE, Hoechst and Dow Chemical). These membranes have pores sizes that prevent ionic substances from diffusing through the membrane. For example, there are nanofiltration membranes that have an ability to reject ions with more than one negative charge (e.g., sulfate and phosphate) while allowing single-charged ions to pass through, with the converse also being the case. In either case, the hollow fiber devices are available in a variety of dimensions and need only be small enough to fit in the replaceable cartridge, which can be sized for use in an in-home system.

In certain embodiments, the sorbent cartridge can further include a flat membrane that is covered with a positively charged material like those described above. In addition, the membrane can be an ion exchange (e.g., anion) membrane that limits the passage of positively charged ions (e.g., Astrom® Neosepta® AFX anion exchange membrane, PCA GmbH PC-SA anion exchange membrane). Advantageously, this ion exchange membrane also has an ability to adsorb phosphate.

The cartridge and/or its components or layers can be replaced (e.g., membrane, urea-degrading enzyme), regenerated (e.g., resin, sorbent) and/or sterilized for re-use when necessary (e.g., saturation, damage, depletion). In addition, the entire cartridge can be replaceable and thus removed from the dialysis system when there is a decrease in the regeneration efficiency of the cartridge (e.g., through layer saturation) or the cartridge becomes worn or damaged, for instance.

Further examples of sorbent cartridges are described in U.S. Pat. No. 6,878,283; U.S. Pat. No. 7,033,498; and in Sorb's REDY cartridge (e.g., see "Sorbent Dialysis Primer" COBE Renal Care, Inc. Sep. 4 1993 Edition, and "Rx Guide to Custom Dialysis" COBE Renal Care Inc. Revision E. September 1993), all incorporated in their entirety by reference herein.

The module 220 is coupled to a hemodialysis machine 30, such as a version of the Fresenius Medical Care 2008K design. In hemodialysis, blood flows through an arterial channel to an arterial pressure sensor. The arterial pressure sensor includes a transducer so that the pressure of the blood flowing through the circuit on the arterial side can be monitored. The blood then flows through a portion of the channel that abuts a pump, such as a peristaltic pump. The pump forces the blood through the circuit. The blood then flows to the dialyzer and then to a venous pressure sensor. The access ports through which blood is removed and returned can be at a convenient and appropriate place on a patient and can be connected to the hemodialysis machine by, any appropriate medical tubing.

While the arterial pressure sensor has been described as being positioned before the pump, in some embodiments, the arterial pressure sensor is after the pump. In certain embodiments, pressure sensors are positioned both before and after the blood pump.

Referring again to FIG. 2, a bypass component 316 is secured to the back 302 of the cartridge holder 300. The bypass component 316 includes ports 318 and 320 that are arranged to receive the fittings 312 and 314 of the base 304 and the arm 306 when the base 304 and the arm 306 are pivoted into engagement with the back 302 (after the sorbent cartridge 24 has been removed from the cartridge holder 300). The bypass component also includes a fluid passage 322 that extends within the back 302 and fluidly connects the ports 318, 320 to one another. The bypass component 316 allows fluid to pass through the cartridge holder 300 even when the sorbent cartridge 24 has been removed from the cartridge holder 300.

Figure 3:
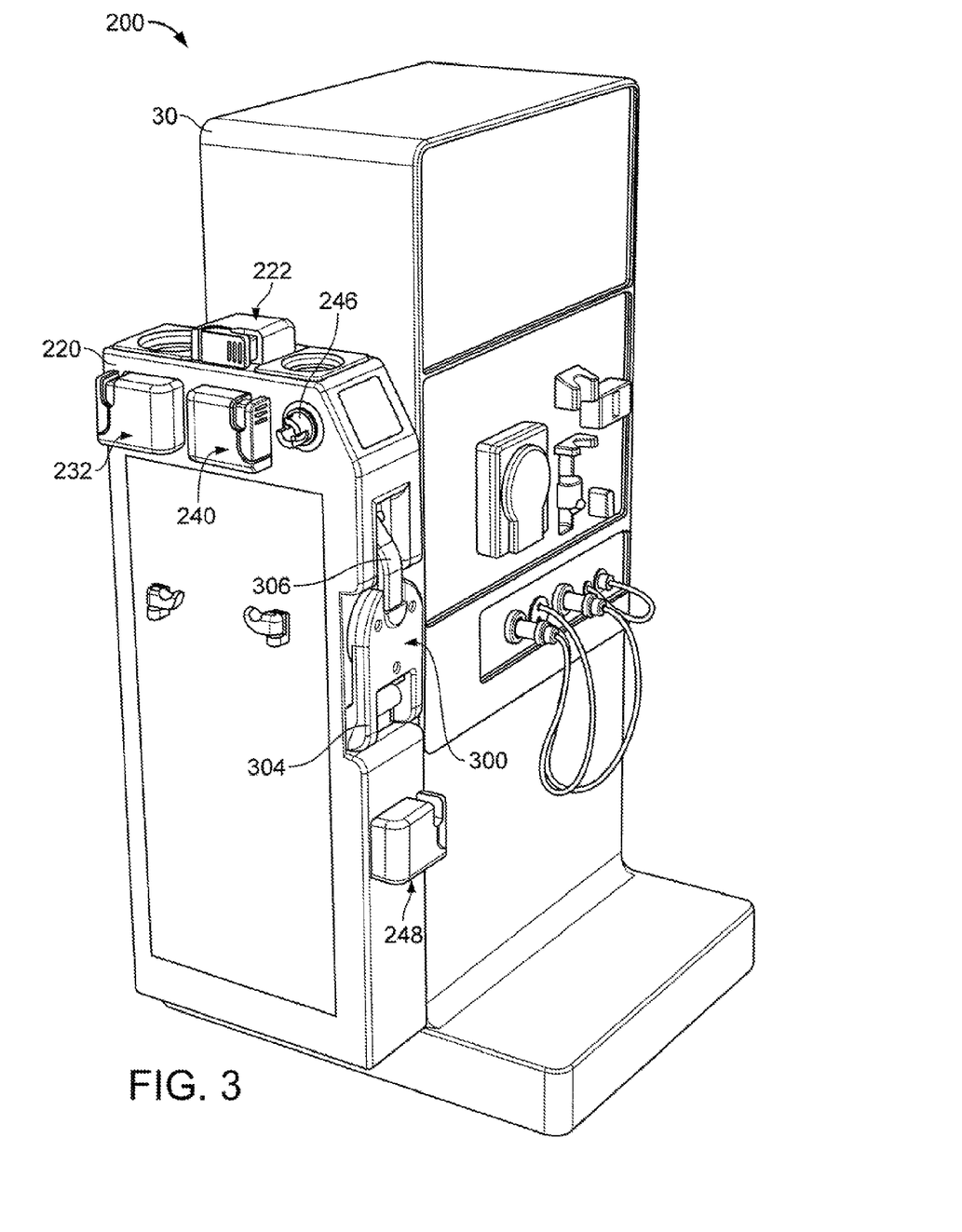
FIG. 3 is a perspective view of the dialysis system of FIG. 1, with the sorbent cartridge removed and the sorbent cartridge holder in a folded configuration.

FIG. 3 shows the system 200 with all external components (e.g., the sorbent cartridge 24, the infusate container 228, the sodium chloride container 230, the bag 238, and their associated fluid lines) disconnected from the module 220 and with the manifolds 222, 232, 240, and 248 and the sorbent cartridge holder 300 in a closed position. When the manifolds 222, 232, 240, and 248 and the sorbent cartridge holder 300 are in their closed positions, they inhibit (e.g., prevent) fluid from exiting the module 220, and thus permit fluid (e.g., a cleaning solution or a rinsing solution) to be circulated in a closed circuit within the module 220 and the dialysis machine 30. Each of the manifolds can, for example, include a member that abuts or extends into fluid line connection ports of the manifolds when the manifolds are in the closed position to create a fluid-tight seal.

Figure 4:
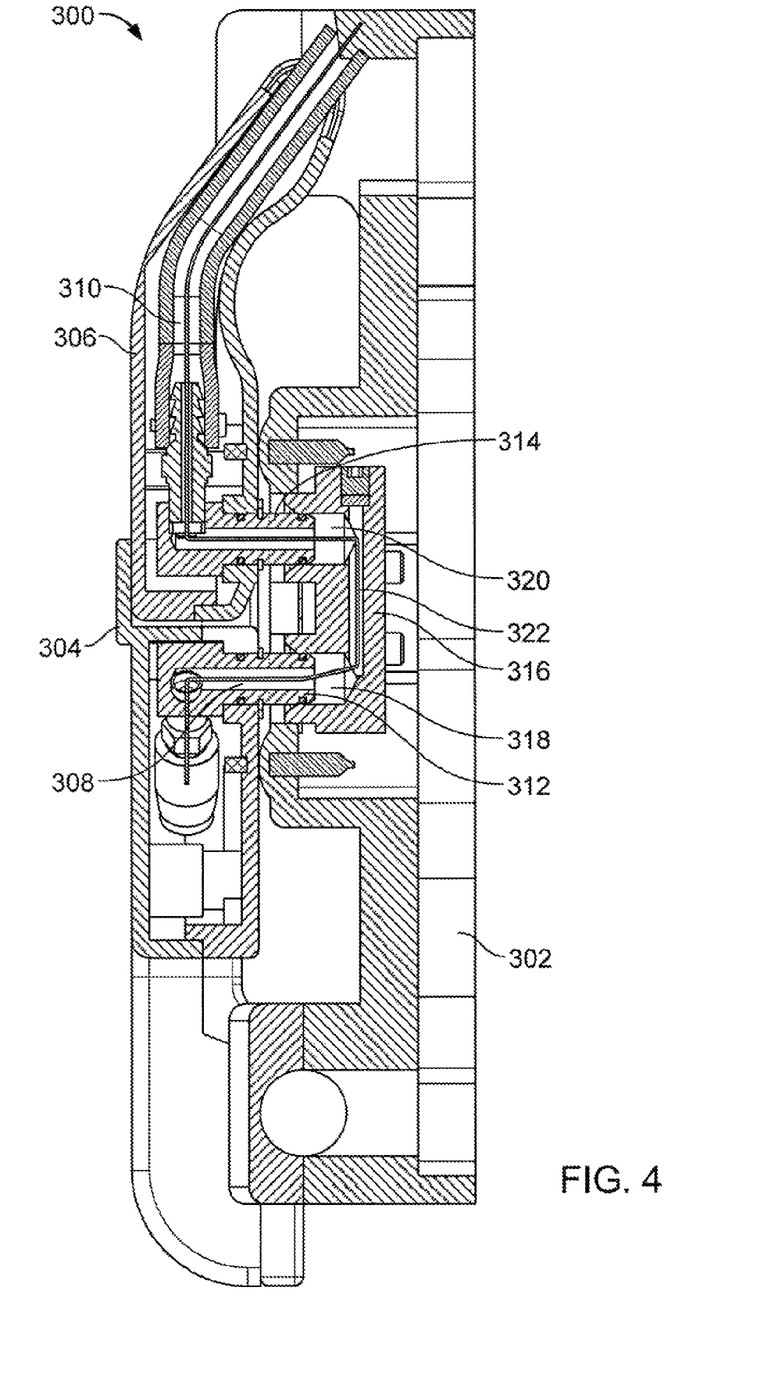
FIG. 4 is a cross-sectional view of the sorbent cartridge holder of FIG. 1 with the sorbent cartridge removed and the sorbent cartridge holder in a folded configuration.

FIG. 4 is a cross-sectional view of the cartridge holder 300 in its folded or closed configuration. Referring to FIGS. 3 and 4, in this folded configuration, the base 304 and the arm 306 are pivoted toward the back 302 and the fittings 312, 314 are disposed in the ports 318 and 320 of the bypass component 316. This configuration permits fluid to pass through the fluid passageway 308 of the base 304 and into a fluid passageway 322 extending through the bypass component 316. The fluid then passes from the fluid passageway 322 of the bypass component 316 to the fluid passageway 310 of the arm 306. Thus, even when the sorbent cartridge 24 has been removed from the cartridge holder 300, a fluid stream can be maintained through the cartridge holder 300.

The external components (e.g., the sorbent cartridge 24, the infusate container 228, the sodium chloride container 230, the bag 238, and their associated fluid lines) are constructed as disposable, single use components and can thus be disconnected from the module 220 and discarded after completion of dialysis treatment. The manifolds and the sorbent cartridge holder 300 can then be closed and a cleaning and/or rinsing solution can be circulated through the module 220 and the dialysis machine 30 to prepare the module 220 and the dialysis machine 30 for a subsequent use.

Figure 5:
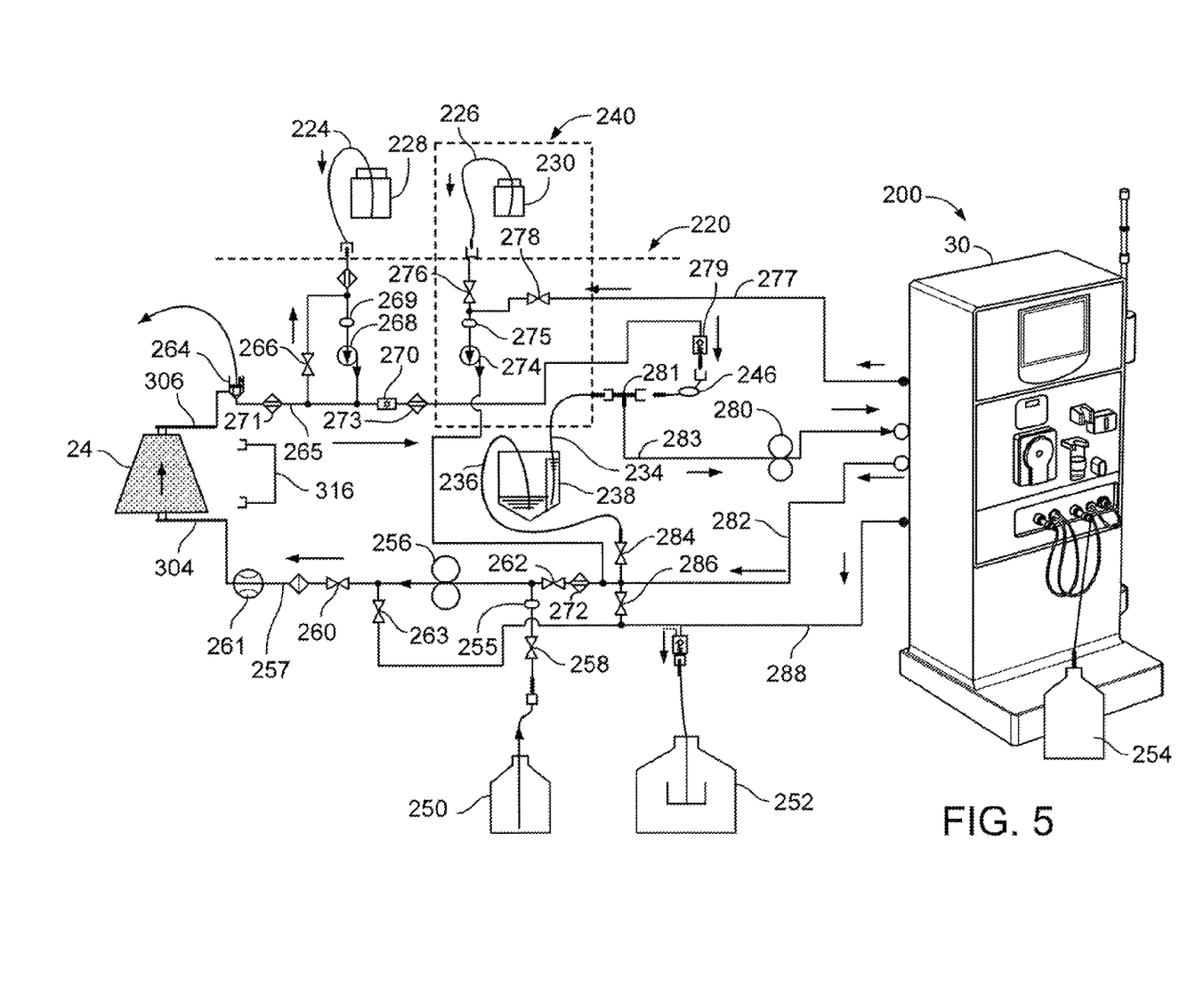
FIG. 5 is a schematic view of the module of FIG. 1, and a front view of the dialysis machine of FIG. 1. The module is configured to introduce sodium chloride solution and/or diluent to dialysate entering the sorbent cartridge.

FIG. 5 is a schematic view of the module 220 coupled to the dialysis machine 30. As shown in FIG. 5, in addition to the external components that have been described as being connected to the module 220, a dialysate bag 250 and a drain bag 252 are also connected to the module 220 via the manifold 248 (shown in FIGS. 1 and 3). In addition, a dilution bag 254 is fluidly connected to the dialysis machine 30.

Still referring to FIG. 5, a method of performing hemodialysis will now be described. Prior to beginning the dialysis treatment, dialysate is drawn from the dialysate bag 250, passed through the sorbent cartridge 24, and routed to the bag 238. This can be done by activating pump 256 with valves 258, 260 opened and valve 262 closed. After exiting the bag 250 and passing through the valve 258, the dialysate passes through a fluid detector 255, which is adapted to detect the presence or absence of fluid within the line. Fluid detectors of this type are available, for example, from Introtek and Cosense. The dialysate is drawn from the bag 250 until the fluid detector 255 detects the absence of fluid in the line, indicating that all of the dialysate has been forced from the bag 250 into the module 220. Upon detecting the absence of fluid in the line, the fluid detector 255 can transmit this information to a control unit (e.g., microprocessor) that can cause the valves and pumps throughout the system to operate in a way to cause the dialysate to recirculate within the module 220 and/or the dialysis machine 30.

Prior to reaching the sorbent cartridge 24, the dialysate passes through a flow meter 261 that is configured to measure the flow rate of the dialysate passing therethrough. A signal representing the flow rate of the dialysate can be transmitted from the flow meter 261 to a control unit (e.g., a microprocessor). As discussed below, the detected flow rate of the dialysate can be used to control metering of the infusate into the dialysate.

As the dialysate passes through the sorbent cartridge 24, certain substances, such as calcium, magnesium, potassium, and sodium may be removed from the dialysate. There is generally no sodium uptake by the cartridge while the dialysate is circulated through module 220 during treatment except during the prime solution circulation and in the initial part of the treatment process. As discussed above, the sorbent cartridge 24 is also adapted to remove toxins, such as urea, from fluid flowing therethrough, but the dialysate from the dialysate bag 250 would generally not contain any urea. Upon exiting the top of the sorbent cartridge 24, the dialysate flows through a bubble trap 264, which helps to ensure that gases within the dialysate are released. With valve 266 closed, the dialysate is then forced through fluid line 265. The infusate solution, which includes magnesium, calcium, and potassium, is then pumped into the fluid line 265 from the infusate solution container 228 by activating a pump 268. The combination of the dialysate and the infusate solution are mixed within a mixing chamber 270.

After exiting the mixing chamber 270, the dialysate continues to flow through the fluid line 265 and passes through a conductivity meter 273. The conductivity meter 273 can estimate, based on the conductivity of the fluid passing therethrough, the concentration of sodium within the fluid. A pump 274 and valves 276, 278 can then be activated in a manner to introduce sodium chloride (e.g., a mixture of sodium chloride and tap water) into the fluid line 257 from the sodium chloride container 230 if the conductivity reading indicates that the sodium level in the dialysate is lower than desired or to introduce dilution water (e.g., tap water) into the fluid line 257 if the conductivity reading indicates that the sodium level in the dialysate is higher than desired. Tap water used as the dilution water is delivered to the dialysate passing through the fluid lines 257 from the bag 254 connected to the dialysis machine 30. The dialysis machine 30 draws the tap water used as dilution water from the bag 254 and delivers it to the module 220 where it passes through a fluid line 277 toward the valve 278. The dilution water can be metered into the fluid line 257 by activating the pump 274 and opening the valve 278. Similarly, the sodium chloride solution can be metered into the fluid line 257 by activating the pump 274 and opening the valve 276.

An advantage of connecting the sodium control system, which includes the sodium chloride container 230, dilution water container 254, and their respective pumping and valve mechanisms 274, 276, 278, to the fluid line 257 upstream of the sorbent cartridge 24 is that tap water can be used to make the sodium chloride solution and tap water can be used as the dilution water. The sorbent cartridge 24 serves to treat both the spent dialysate received from the dialysis machine 130 and the tap water added into the spent dialysate for dilution control. Sodium control systems that are connected to a dialysate circuit downstream of a sorbent cartridge typically require the use of purified water (e.g., AAMI water) for preparation of sodium chloride solution and for the dilution water because the dialysate circuit generally includes no additional filters capable of purifying water between the sorbent cartridge and the dialyzer where the dialysate contacts the patient's blood. Thus, such systems typically require the storage and use of large volumes of purified water. By permitting the use of tap water in the sodium chloride solution and the dilution water, the module 220 greatly reduces the amount of purified water that the patient must store and use. In some cases, tap water is also used to make the dialysate that is used with the system 200. In those cases, the sorbent cartridge 24 is used to filter the tap water of the dialysate in the same way that the sorbent cartridge 24 is used to filter the tap water found in the sodium chloride solution and the dilution water. As a result, the system 200 can be operated with little or no pre-packaged purified water.

Prior to reaching the fluid lines 265 and 257, the infusate solution and the sodium chloride solution pass through fluid detectors 269 and 275, which can detect the presence or absence of fluid. The fluid detectors 269, 275 can be similar in construction to the fluid detector 255 discussed above.

A microprocessor is used to control the pumps 268, 274 and the valves 276, 278. The microprocessor is connected to flow meter 261, the conductivity meter 273, the pumps 268, 274, and the valves 276, 278. The measured flow rate of the dialysate is transmitted in the form of a signal from the flow meter 261 to the microprocessor. The microprocessor controls the pump 268 as a function of the flow rate of the dialysate measured by the flow meter 261. This arrangement helps to ensure that a desired amount of the infusate is added to the dialysate, and thus helps to ensure a desired proportion of the infusate to the dialysate. The conductivity reading is similarly sent in the form of a signal from the conductivity meter 273 to the microprocessor, and, in response, the microprocessor sends signals to the pumps 268, 274 and the valves 276, 278 to cause the infusate solution to be introduced into the fluid line 265, and to cause the sodium chloride solution and/or the dilution water to be introduced into the fluid line 257.

The microprocessor is also connected to the fluid detectors 269, 275. Upon detecting an absence of fluid within their respective lines, the fluid detectors 269, 275 can transmit a signal to the microprocessor, which can shut down the system or provide an indication (e.g., an audible and/or visual indication) to the user that the infusate container 228 and/or the sodium chloride container 230 are empty. In response, the user can, for example, replace or refill the infusate container 228 and/or the sodium chloride container 230.

After passing through the conductivity meter 273, the dialysate passes through a check valve 279 and into the ammonium sensor 246, which detects ammonium levels within the dialysate. If the ammonium levels within the dialysate are within an acceptable range, the dialysate is allowed to flow into the bag 238.

After filling the bag 238 to a desired level with dialysate having a desired concentration of calcium, magnesium, potassium, and sodium, a pump 280 is activated to draw the dialysate from the bag 238 into the dialysis machine 30. The dialysate is circulated through the dialysis machine 30 where it passes through a dialyzer. At the same time, a patient's blood is passed through the dialyzer. As a result, toxins, such as urea, are transferred across a permeable membrane of the dialyzer from the patient's blood to the dialysate. The spent dialysate exiting the dialyzer is then routed back to the module 220.

The spent dialysate passes through a fluid line 282 in the module 220. Depending on the desired volume of dialysate to be cycled back to the dialysis machine, some of the spent dialysate can be routed to the bag 238 by opening a valve 284 and closing a valve 286 as the spent dialysate is forced through the fluid line 282. As a result of the dialysis, for example, fluid from the patient may be added to the dialysate as the dialysate passes through the dialyzer of the dialysis machine 30. Thus, routing some of the spent dialysate to the bag 238 can help to ensure that a substantially constant volume of dialysate is circulated through the module 220 and the dialysis machine 30 throughout treatment. The pump 256 in the fluid line 282 forces the volume of the spent dialysate that is not routed to the bag 238 into the sorbent cartridge 24 via the base 304 of the cartridge holder 300. As the spent dialysate passes through the sorbent cartridge 24, urea is removed from the spent dialysate. Calcium, magnesium, and potassium are also stripped from the spent dialysate by the sorbent cartridge 24. The recycled dialysate or cartridge effluent, upon exiting the sorbent cartridge 24, passes through the bubble trap 264 where gases that may be produced as a result of chemical reactions within the sorbent cartridge 24 can be removed from the recycled dialysate. In the manner discussed above, after the recycled dialysate exits the sorbent cartridge 24, the infusate solution is introduced into the recycled dialysate and based on the conductivity reading at the conductivity meter 273, sodium chloride or dilution water can be added to the recycled dialysate at the fluid line 257. In the initial stages of treatment, sodium levels in the recycled dialysate tend to be lower than desired due to the sorbent cartridge's tendency to strip sodium from fluids passing therethrough. Consequently, in the early stages of the treatment, sodium chloride will typically be injected into fluid line 257 to increase the concentration of sodium in the recycled dialysate. In later stages of the treatment, however, the sorbent cartridge may contain higher levels of sodium and thus start releasing sodium into the spent dialysate as it passes through the sorbent cartridge. This can lead to higher than desired levels of sodium in the recycled dialysate passing through the fluid line 265, resulting in an injection of dilution water into the recycled dialysate.

The conductivity meter 273 is used to monitor the infusion of dilution water or sodium chloride solution into the dialysate to ensure that the conductivity of the dialysate at the output of the module 220 is within a desired range. For example, the amount of dilution water added is determined based on the contribution to dialysate conductivity by 1) sodium released by the sorbent cartridge 24, 2) the amount of infusate added to the fluid line 265 and 3) the amount of sodium added to the fluid line 257 from the sodium container 230. The conductivity contribution from the sodium released by the sorbent cartridge 24 is determined by the difference between the readings of conductivity meters 271 and 272. The conductivity contribution from the infusate is determined by the differences in reading between conductivity meters 271 and 273. For example, if the desired conductivity at the output of the module 220 is 14 mS/cm, and the sorbent cartridge contributes a conductivity of 0.13 mS/cm, and the infusate contributes a conductivity of 0.5 mS/cm, then dilution water is added to the dialysate in the fluid line 257 so that a reading of 13.37 mS/cm is obtained at the conductivity meter 272.

The recycled dialysate, after exiting the conductivity meter 273, then passes through the check valve 279 and into the ammonium sensor 246. The ammonium sensor 246 can help to determine the state of the sorbent cartridge 24. For example, as the sorbent cartridge 24 is used, the ammonium levels in the dialysate will increase. Upon reaching a predetermined ammonium level, the treatment can be terminated. Alternatively, upon reaching the predetermined ammonium level, the sorbent cartridge 24 can be replaced with a fresh sorbent cartridge and treatment can resume.

After exiting the ammonium sensor, the recycled dialysate is routed to the bag 238 and/or the dialysis machine 30. For example, in order to ensure that an equal amount of fluid enters and exits the dialysis machine 30, a T-valve 281 can be adapted to route a portion of the dialysate to the dialysis machine 30 via fluid line 283 and to route any excess dialysate to the fresh dialysate chamber of the bag 238. If the flow rate of the dialysate at the T-valve 281 is greater than the rate at which the dialysate is being pulled into the dialysis machine 30, some of the dialysate will be routed to the bag 238. If, on the other hand, the flow rate of the dialysate at the T-valve 281 is less than the rate at which the dialysate is being pulled into the dialysis machine 30, the dialysis machine 30 will pull some of the dialysate from the bag 238. The bag 238 is formed of a flexible material and thus acts as a compliance chamber. In particular, as the dialysate is added to the bag 238, the volume of the bag 238 is allowed to increase, and, as the dialysate is removed from the bag 238, the volume of the bag 238 is allowed to decrease.

The dialysate that is delivered to the dialysis machine 30 again passes through the dialyzer where toxins are transferred from the patient's blood to the dialysate. The spent dialysate is then routed back to the module and the process is repeated until a desired amount of toxins has been removed from the patient's blood.

During treatment, an ultrafiltration process may also be performed to remove water from the patient's blood. During ultrafiltration, a pressure gradient is created across the membrane between the dialysate side and the blood side of the dialyzer. As a result, fluid is drawn across the membrane from the blood side to the dialysate side. This fluid exits the dialysis machine 30 and passes though the module 220 via a fluid line 288 and is routed to a drain bag 252. This ultrafiltration process can be continued until a desired volume of fluid has been removed from the patient.

After completing the patient's treatment, the dialysate can be removed from the bag 238. For example, the pump 256 can be activated with the valves 262, 263, 284 open and the valves 260, 286 closed. As a result, the dialysate flows from the bag 238 into the drain bag 252. Emptying the bag 238 can allow the user to more easily handle the bag 238 after treatment due to the decreased weight. In some cases, eight liters or more of dialysate is removed from the bag 238 prior to disconnecting the bag 238 from the module 220.

After draining the bag 238 to a desired level, the external components (e.g., the sorbent cartridge 24, the infusate container 228, the sodium chloride container 230, the bag 238, the dialysate bag 250, and their associated fluid lines) are disconnected from the module 220 and discarded. The manifolds 222, 232, and 230 (shown in FIGS. 1 and 3) to which the sorbent cartridge 24, the infusate container 228, the sodium chloride container 230, and the bag 238 were fluidly connected are closed so that fluid cannot flow out of the module 220 through the fluid line connection ports of the manifolds 222, 232, and 230. A bag of rinsing solution is then connected to the fluid connection port of the manifold 248 (shown in FIGS. 1 and 3) where the dialysate bag 250 was previously connected, and rinsing solution (e.g., water) is circulated through the module 220 and the dialysis machine 30 to rinse the fluid conduits within the module 220 and the dialysis machine 30. The rinsing process is carried out by drawing the rinsing solution from the rinsing solution bag into the fluid line 282 by activating the pump 256 with valves 258 and 260 open. The rinsing solution moves along the fluid line 282 to the cartridge holder 300, which is in a closed configuration (with the sorbent cartridge 24 removed) such that the fittings on the base 304 and the arm 306 of the cartridge holder are connected to the ports 318 and 320 of the bypass component 316, as shown in FIGS. 3 and 4. The various pumps and valves of the module 220 and the dialysis machine 30 are then activated in a manner to cause the rinsing solution to pass through the various fluid conduits of the module 220 and the dialysis machine 30. The rinsing solution can be collected in the drain bag 252 after passing through the various desired fluid conduits of the module 220 and the dialysis machine 30.

As an alternative to or in addition to passing the rinsing solution through the module 220 and the dialysis machine 30, a cleaning solution (e.g., bleach) can be circulated though the module 220 and the dialysis machine 30 in a similar manner to disinfect the various fluid conduits of the module and the dialysis machine.

In certain embodiments, a fluid (e.g., a rinsing solution, a cleaning solution, or dialysate left in the fluid conduits of the module 220 and the dialysis machine 30 after treatment) can be passed through the dialysis machine 30 where it is heated to a temperature of about 85 degrees Celsius. The heated fluid can be circulated through the module 220 and the dialysis machine 30 to disinfect the fluid conduits within those devices.

While certain embodiments have been described, other embodiments are possible.

In some embodiments, the bag 238 is connected to the bubble trap 264 via an additional fluid line extending from the portion of the bag 238 that contains spent dialysate to the bubble trap 264. In such embodiments, the fluid line 283 that leads to the dialysis machine 30 can extend into the portion of the bag 238 containing the fresh dialysate instead of being connected to the T-valve 281. During use, fresh dialysate is first forced into the fresh dialysate chamber of the bag 238, and then in a subsequent action the fresh dialysate is drawn from the bag 238 into the dialysis machine 230 via the fluid line 283. Because the pressure is regulated within the bag 238 as a result of the bag's connection to the bubble trap, the check valve 279 prior to the ammonium sensor 246 can be removed from the fluid loop.

While the external components (e.g., the sorbent cartridge 24, the infusate container 228, the sodium chloride container 230, the bag 238, the dialysate bag 250, the drain bag 252, the rinsing solution bag, the cleaning solution bag, and their associated fluid lines) connected to the module 220 have been described as being disposable, single use disposable components, one or more of the external components can alternatively be reusable. For example, they can be constructed to withstand disinfection techniques, such as autoclave disinfection.

While the module 220 has been described as being connected to the drain bag 252 via the manifold 248, the module can alternatively or additionally be connected directly to a drain via the manifold 248.

While the system 200 has been described as being initially primed with dialysate from the dialysate bag 250, the system can alternatively or additionally be attached to a water source (e.g., a water tap) and can be adapted to convert water (e.g., tap water) from the water source into dialysate. In certain embodiments, for example, the dialysis machine 30 is adapted to spike the water passing therethrough with one or more concentrates to form dialysate. Because the water is passed through the sorbent cartridge 24 prior to entering the dialysis machine 30, impurities in the water will be filtered by the sorbent cartridge 24 prior to contacting the patient's blood in the dialyzer of the dialysis machine 30.

While certain methods described above include controlling the rate at which the infusate solution is introduced into the fluid line 265 based on the flow rate of the dialysate detected at the flow meter 261, other techniques are possible. In certain embodiments, for example, the weight of the infusate container 228 and the weight of the dialysate bag 238 are measured (e.g., be a weight scale), and the flow rate of the infusate is controlled based on these readings. In certain embodiments, the weight of the drain bag 252 can also be measured and accounted for when determining the appropriate flow rate of the infusate solution.

While the module 220 has been described as including pumps 268, 274 for moving the infusate solution and the sodium chloride solution from their respective containers to the fluid lines 265 and 257, other techniques can alternatively or additionally be used. In certain embodiments, for example, a vacuum is used to draw the infusate solution and the sodium chloride solution from their respective containers into the fluid lines. The flow rate of the dialysate within the fluid line 265 can, for example, create a vacuum that draws the infusate solution into the fluid line 265. In some embodiments, venturi tubes are provided along the fluid line 265 at the locations where the line extending from the infusate solution container 228 joins the fluid line 265. The venturi tubes can help to ensure that a sufficient vacuum is created to draw the infusate solution into the fluid line 265 from the infusate container 228. In embodiments that use a vacuum to draw the solutions from their respective containers, a valve can be provided within the lines leading from the infusate solution container 228 and the sodium chloride solution container 230 to control the flow rates of the infusate solution and the sodium chloride solution into the fluid lines 265, and 257, respectively. These valves can be connected to and controlled by the microprocessor in the module 220.

Figure 6:
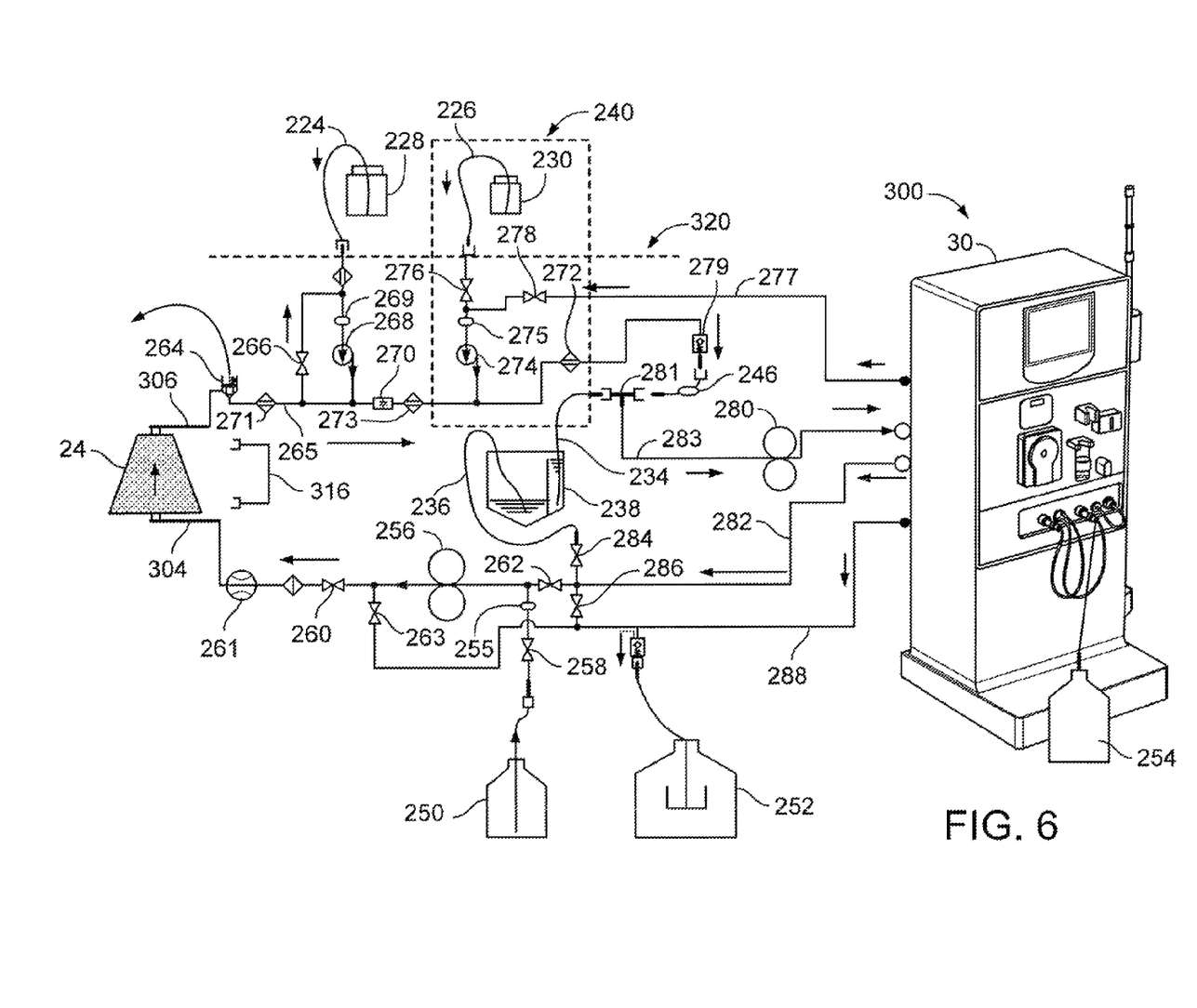
FIG. 6 is a schematic view of a module of a dialysis system, and a front view of a dialysis machine of the dialysis system. The module of the dialysis system is configured to introduce sodium chloride solution and/or diluent to dialysate exiting a sorbent cartridge of the module.

While the sodium control system 240 of the module 220 has been described as being connected to the fluid line 257 upstream of the sorbent cartridge 24, in certain embodiments, the sodium control system 240 is arranged to introduce sodium chloride solution and/or dilution water into the dialysate circuit at a point downstream of the sorbent cartridge 24. FIG. 6 schematically illustrates an example of such a system 300. As shown in FIG. 6, the system 300 includes a module 320 that closely resembles the module 220 described above. However, in the module 320, the sodium control system 240 is connected to the fluid line 265 downstream of the sorbent cartridge 24. Because the sodium chloride solution and dilution water is not passed through the sorbent cartridge 24 prior to passing through the dialyzer 30 and contacting the patient's blood in this system, purified water (e.g., AAMI water) is used to make the sodium chloride solution and the dilution water. The system 300 otherwise works in generally the same manner as the system 200 described above.

As an alternative to or in addition to the sodium control system 240 described above, other types of sodium control systems can be used. In certain embodiments, for example, dilution reservoirs can be used to control the concentration of an electrolyte, such as sodium. The dilution reservoir can be of any size or shape that enables the reservoir to retain a volume of fluid that is sufficient to provide dilution of the fluid circulating through the components of the system. Typically, the diluent contained in the dilution reservoir is water. Once the dilution reservoir is filled, the dialysate is directed to the dialysis machine 30 where it is spiked with a known concentrated (either liquid or powder form) to attain a base sodium and bicarbonate level. This spiking process can be carried out manually or automatically. At this time, fluid continues to be recirculated through the dialysis machine 30 and the module 220.

The system for controlling sodium can alternatively or additionally be adapted to increase sodium levels in the fluid passing through the system. For example, a system for controlling sodium can include a container containing a concentrated sodium solution in addition to the dilution reservoir. A flow pump 60 can serve to infuse the concentrated sodium solution or the dilution volume into the dialysate. As described, the sodium concentrate can be used to adjust and manipulate the sodium levels in the dialysate and can thus be used to adjust and manipulate a patient's sodium levels.

Other devices that do not involve adding a diluent (e.g., tap water) to the fluid circulating through the system can alternatively or additionally be used to control sodium levels within the circulating fluid. For example, a system for controlling sodium can include a column containing a strong acid/strong base resin combination that can be used to remove sodium from the fluid circulating through the system. The column can be formed from a replaceable cartridge. Alternatively, the column can be formed from a deionization polisher. The strong acid/strong base resin combinations can remove sodium from the dialysis solution and control pH. A three-way valve can be used is fluidly connected to the dialysate to the column. Upon detecting excessive sodium levels within the fluid circulating through the system, the three-way valve can be used to divert the effluent from the sorbent cartridge through the strong acid/strong base ion exchange resin mixture in the column to remove sodium in exchange for water. Advantageously, this method allows sodium levels to be adjusted without the addition of water to the fluid circulating through the system. Thus, additional reservoir volume is not required to compensate for the dilution. An exchange program may be used to regenerate the deionization polisher. The control method for either the dilution or the ion exchange systems could be via electronic feedback from the hemodialysis machine, a separate conductivity probe or a timed sequence. Further information regarding alternative sodium control systems can be found in U.S. Patent Application Publication No. 2009/0127193, which is incorporated by reference herein.

In addition to the components discussed above, the module of the dialysis system can further include various fluid detectors to confirm that fluid is passing through a particular fluid line or component at a desired time, flow meters to help ensure that fluid is passing through a particular fluid line or component at a desired rate, and filters to filter fluid passing through a particular fluid line or component. In certain embodiments, these additional components can be connected to the microprocessor of the module such that other components, such as pumps and valves, of the module can be adjusted based on the readings of these additional components.

While the systems described above use the sorbent cartridge 24 to remove toxins from the spent dialysate, other types of devices can alternatively or additionally be used to remove toxins from the spent dialysate.

While the modules described herein have been described as being coupled to the dialysis machine 30, other arrangements are possible. In some embodiments, for example, the module is incorporated into the dialysis apparatus. Alternatively, the module can be a stand-alone unit.

While certain devices and methods disclosed herein have been described as being used in conjunction with hemodialysis, they can be used in various other renal treatments. The principles described herein can be applicable to the particular type of hemodialysis apparatus described herein, and to a variety of other dialysis apparatus having similar functions.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

Other embodiments are within the scope of the following claims.

What is claimed is:
1. A dialysis system, comprising:
 a module that is connected to a dialysis machine, the module comprising:
 a device adapted to remove one or more substances from a dialysis solution as the dialysis solution passes through the device;
 a foldable holder configured to retain the device in a manner such that the dialysis solution can pass through the device;
 a fluid line in fluid communication with the device;
 a sodium control system in fluid communication with the fluid line, the sodium control system being adapted to alter a sodium concentration of dialysis solution passing through the fluid line;
 a first container that stores a diluent, the diluent being stored separately from an infusate solution that provides at least a portion of the dialysis solution;
 a first pump that moves dialysis solution from the module into the dialysis machine;
 a second pump that moves diluent from the first container into the module; and
 a processor configured to control the first pump to move dialysis solution from the module into the dialysis machine and configured to control the second pump to move diluent from the first container into the module.

2. The dialysis system of claim 1, wherein the fluid line is arranged so that solution exiting the fluid line enters the device.

3. The dialysis system of claim 1, wherein the fluid line is arranged so that solution exiting the device enters the fluid line.

4. The dialysis system of claim 1, wherein the sodium control system is adapted to introduce the diluent into the fluid line.

5. The dialysis system of claim 4, wherein the diluent comprises tap water.

6. The dialysis system of claim 4, wherein the sodium control system comprises the first container that contains the diluent, and the sodium control system further comprises the second pump of the module, the second pump arranged to move the diluent from the first container to the fluid line.

7. The dialysis system of claim 1, wherein the sodium control system is adapted to introduce sodium into the fluid line.

8. The dialysis system of claim 7, wherein the sodium is in the form of a sodium chloride solution.

9. The dialysis system of claim 7, wherein the sodium control system comprises a second container that contains a sodium solution, and the sodium control system further comprises the second pump of the module, the second pump arranged to move the sodium solution from the second container to the fluid line.

10. The dialysis system of claim 9, wherein the sodium control system further comprises the first container that contains the diluent, and the second pump is arranged to move the diluent from the first container to the fluid line.

11. The dialysis system of claim 10, wherein the sodium control system further comprises one or more valves that can be actuated to control movement of the sodium solution and the diluent to the fluid line.

12. The dialysis system of claim 1, further comprising a conductivity meter that is adapted to measure conductivity of the solution passing through the fluid line, the conductivity meter being in communication with the sodium control system.

13. The dialysis system of claim 12, wherein the sodium control system is adapted to alter the sodium concentration of the solution passing through the fluid line based on an output signal of the conductivity meter.

14. The dialysis system of claim 1, wherein the device comprises a sorbent cartridge.

15. The dialysis system of claim 14, wherein the sorbent cartridge comprises at least one layer of material capable of regenerating spent dialysis solution.

16. The dialysis system of claim 15, wherein a layer of the sorbent cartridge comprises sodium zirconium carbonate.

17. A dialysis system, comprising:
a dialysis machine; and
a module that is configured to be releasably, fluidly coupled to the dialysis machine, the module comprising:
a device adapted to remove one or more substances from a dialysis solution as the dialysis solution passes through the device after exiting the dialysis machine,
a foldable holder configured to retain the device in a manner such that the dialysis solution can pass through the device,
a sodium control system that is adapted to alter the sodium concentration of the dialysis solution, the sodium control system being arranged to alter the sodium concentration of the dialysis solution before the dialysis solution passes through the device,
a container that stores a diluent, the diluent being stored separately from an infusate solution that provides at least a portion of the dialysis solution;
a first pump that moves dialysis solution from the module into the dialysis machine,
a second pump that moves diluent from the container into the module, and
a processor configured to control the first pump to move dialysis solution from the module into the dialysis machine and configured to control the second pump to move diluent from the container into the module.

18. The dialysis system of claim 17, wherein the dialysis machine is a hemodialysis machine.

19. The dialysis system of claim 17, wherein the device comprises a sorbent cartridge.

* * * * *

UNITED STATES PATENT AND TRADEMARK OFFICE
CERTIFICATE OF CORRECTION

PATENT NO. : 8,889,004 B2  
APPLICATION NO. : 12/844968  
DATED : November 18, 2014  
INVENTOR(S) : Updyke et al.

It is certified that error appears in the above-identified patent and that said Letters Patent is hereby corrected as shown below:

On the title page, item [56]

On page 2, column 2, line 1, after Other Publications, delete "Pimer" and insert --Primer--.

On page 2, column 2, line 2, after Other Publications, delete "Artif Organs" and insert --Artificial Organs--.

Signed and Sealed this
Seventh Day of April, 2015

Michelle K. Lee
*Director of the United States Patent and Trademark Office*